United States Patent [19]

Zabel

[11] 4,323,092

[45] Apr. 6, 1982

[54] APPARATUS AND PROCESS FOR DETECTING FREE CHLORINE

[75] Inventor: Bernd G. Zabel, Rottweil, Fed. Rep. of Germany

[73] Assignee: Corvinus & Roth GmbH, Altenstadt, Fed. Rep. of Germany

[21] Appl. No.: 188,607

[22] Filed: Sep. 19, 1980

[51] Int. Cl.³ .......................................... G05D 11/08
[52] U.S. Cl. ........................................ 137/5; 75/165; 137/93; 204/293; 210/96.1; 210/169; 210/743
[58] Field of Search .................. 75/165; 137/5, 93; 204/293; 210/96.1, 169, 743, 746; 324/425, 439, 444, 446

[56] References Cited

U.S. PATENT DOCUMENTS

| | | | |
|---|---|---|---|
| 2,370,871 | 3/1945 | Marks | 324/439 X |
| 2,851,655 | 9/1958 | Haddad | 324/444 |
| 3,222,264 | 12/1965 | Nesh | 324/439 X |
| 3,430,129 | 2/1969 | Cardeiro | 324/439 |
| 3,956,094 | 5/1976 | Capuano | 324/425 X |
| 4,005,004 | 1/1977 | Seko | 204/290 F |
| 4,033,871 | 7/1977 | Wall | 137/5 X |
| 4,127,468 | 11/1978 | Alfenaar | 204/293 X |

FOREIGN PATENT DOCUMENTS 2203025 8/1973 Fed. Rep. of Germany ........ 75/165

*Primary Examiner*—Robert G. Nilson
*Attorney, Agent, or Firm*—Mortenson & Uebler

[57] ABSTRACT

Apparatus and process are provided for measuring and monitoring the free active chlorine content of an aqueous solution. Regulation of the addition of chlorinating substances to maintain a desired chlorine level in drinking or bathing water is further provided. The apparatus preferably utilizes a measuring cell having electrodes comprised of a gold-nickel metallic alloy wherein gold is contained in an amount 90–97% by weight and nickel in an amount of 10–3% by weight. The measuring cell is connected to an electrical comparison circuit which controls a regulator or magnetic valve, in order to control the flow of active chlorine into the system.

6 Claims, 1 Drawing Figure

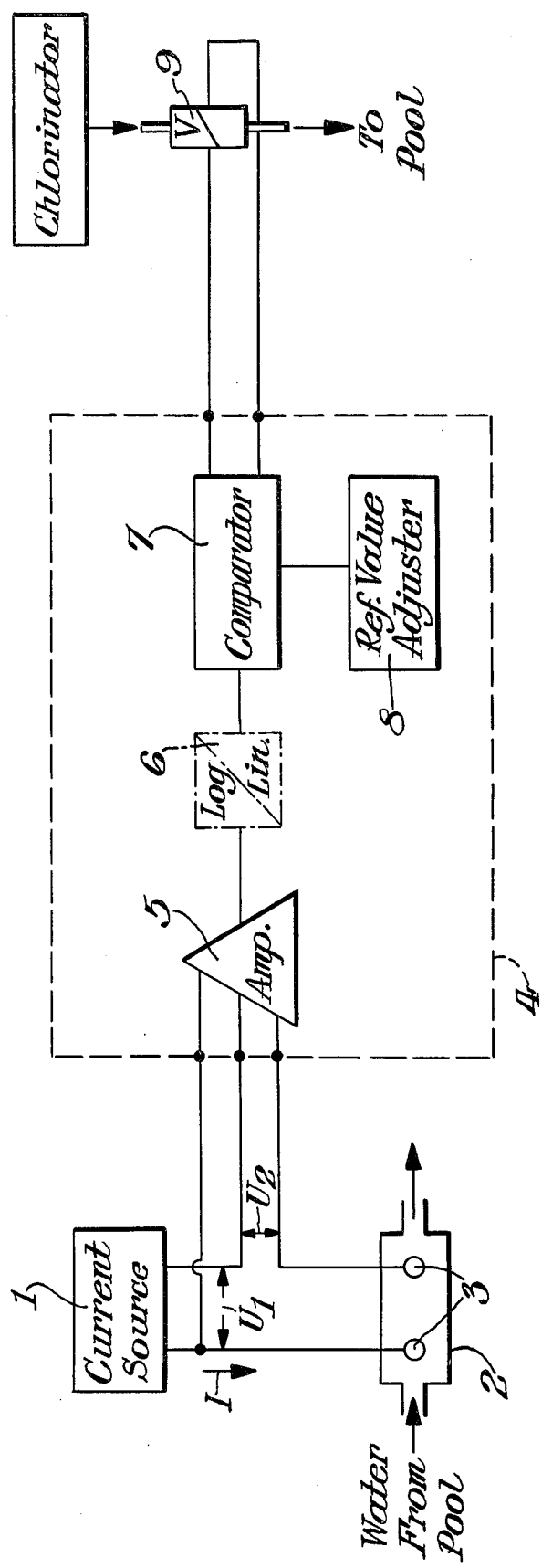

APPARATUS AND PROCESS FOR DETECTING FREE CHLORINE

BACKGROUND OF THE INVENTION

1. Field of Invention

This invention relates to a device that provides for a constant chlorine content in water. In particular, a simple, easily manipulated sensing electrode is provided that enables continuous monitoring of the free chlorine content of water. Electronic circuitry is provided for regulating chlorine additives to provide a desired content. Further, the device exhibits a very low transverse sensitivity to other materials which may be contained in water.

2. Description of the Prior Art

Because water used for drinking and bathing is primarily sterilized by chlorine, several methods have been developed to measure the free active chlorine content in aqueous solutions. The most widely used measurement means is the DPD method. Here, a chemical (diethyl-p-phenyldiamine) is added to a water sample contained in a standard measuring vessel and the sample color is compared to a color scale graduated in concentration steps.

The above technique can be automated. One device takes in water samples by means of a pump system. These samples are divided into two partial streams by means of an overflowing vessel, a so-called flow-through cuvette. One partial stream is mixed with a small, exactly defined quantity of a reagent and is transferred to the analysis cuvette. The second, untreated water sample is fed into a reference cuvette parallel to the treated sample cuvette. A zero-point adjustment is performed continuously and automatically. The reddish color of the treated sample water is measured and compared with the untreated water sample by a double beam photometer, and chlorine addition is adjusted accordingly.

Another prior art device uses the continuous through-flow analysis principle. Here a constant stream of sampled water flows out of a flow-through apparatus included in a mixer unit. Two impeller type pumps meter a buffered solution and a DPD-sulfate solution. When free chlorine is present, the concentration is indicated by a proportional amount of dye that is evaluated in a photometer attached to the measuring apparatus. A maximum of one minute response time elapses between the taking of the sample and the indication of the evaluated result. The measured value is read by a calibrated meter and additionally the measured value output provides a signal for continuous recording by a chart recorder.

With both of the above devices, the measured value at a given time can be converted to an electrical value and, by comparison with a reference value, regulation can be accomplished.

Electronic measuring procedures are also known. In a known arrangement, water flows past two electrodes made of two different metals and with these electrodes the water forms a voltaic cell. So long as the water contains no free active chlorine, the voltaic cell is substantially polarized. It delivers only a very low electrical current, termed residual current, for which electrical compensation is made. When free active chlorine is present, the polarization is disturbed. The voltaic cell becomes depolarized and delivers an electrical current whose magnitude is proportional to the concentration of free active chlorine. The electrode materials in the prior measurement cell are platinum and copper. Because the copper surface is subject to oxidation, quartz sand is placed within the measurement cell to act as a scouring agent. Due to the water circulation, the sand is kept in agitation and scours the electrodes so the copper electrode always presents a chemically clean surface. The device is calibrated after running idle for several hours by comparison with a DPD-measurement. The zero-point and measurement range adjustments must be redone approximately once a week as a routine scheduled monitoring of performance.

Another electronic method exists that operates according to the "Diffusion Limit-Current Method". Here a determined value of a unipotential voltage is applied to the operating electrode that is at a potential somewhat above the reduction potential of the ions to be displaced (in this case $ClO^-$ ions). At the electrode, stray $ClO^-$ ions are discharged. This results in a flow of electrical current. The stray ions following and coming from the adjacent medium maintain a flow of current, also termed "diffusion current", that is proportional to the concentration of free chlorine in the system. This measurement procedure is appropriate for stationary sample solutions. As a consequence of the requirements, the chlorine measurements in swimming pools and in potable water must have a continuous through-flow of the water being measured; the apparatus must have a device (i.e. pump) that produces an extremely constant flow. This method depends on the extreme accuracy of the polarization voltage. The polarization voltage and the electrode material determine the selectivity and, therefore, the accuracy of the device. Also, this method demands extremely expensive apparatus and is difficult to manipulate and handle.

The present invention relates to a metallic alloy, chlorine sensing electrode. Many patents have been issued concerning metal alloys used in electrodes. U.S. Pat. No. 4,127,468 discloses a metal electrode of a basis metal which is present in a finely divided or porous state and an alloying element. For the basis metal, any of the metals or their alloys from the Groups VIII, IB and IIB of the Periodic Table of Elements is used. The alloying-element is one selected from the groups IIIA IVA, VA, VIA, VIII, IB, IIB, or VIIIB of the Periodic Table of Elements.

U.S. Pat. No. 4,005,004 discloses an electrode used as an anode for electrolysis of an aqueous sodium chloride solution comprising an anti-corrosive conductor having a coating of a solid solution containing at least one noble metal oxide together with titanium oxide and zirconium oxide.

SUMMARY OF THE INVENTION

An electrode is provided for use in detecting free chlorine in aqueous media comprising an alloy of gold and a metal selected from the group consisting of nickel, copper or iron, wherein gold is contained in an amount of about 90% to about 97% by weight and nickel, copper or iron is contained in an amount of about 10% to about 3% by weight. The preferred electrode is one wherein the gold content is about 95% and the second metal is nickel in an amount of about 5%.

Also provided are apparatus and a process for measuring and monitoring the free chlorine content of aqueous solutions using the above electrode comprising a current source providing current directed to at least two electrodes contained in a measuring cell through which a sample of the aqueous solution is flushed, at least one of the electrodes being of the composition of the above electrode, the output signal from the electrodes being proportional to the free chlorine content of the aqueous solution, the signal being amplified by an amplifier, the amplifier output being sent to an optional linearization circuit, then to a comparator for comparison with a reference signal provided by a reference value adjuster, the difference in value of the measured signal and reference value being proportional to the free chlorine content in the aqueous system, the difference being used to adjust a regulating valve which adjusts the flow of additional chlorine to the aqueous solution.

BRIEF DESCRIPTION OF THE DRAWING

The accompanying drawing is a schematic diagram of an electronic circuit utilizing the electrodes of this invention in a system for continuously monitoring and regulating the addition of chlorine to aqueous systems such as in swimming pools.

DETAILED DESCRIPTION OF THE INVENTION AND PREFERRED EMBODIMENTS WITH REFERENCE TO THE DRAWING

Apparatus and process are provided for measuring and monitoring the free active chlorine content of an aqueous solution. Regulation of the addition of chlorinating substances to maintain a desired chlorine level in drinking or bathing water is further provided. The apparatus preferably utilizes a measuring cell having electrodes comprised of a gold-nickel metallic alloy wherein gold is contained in an amount 90-97% by weight and nickel in an amount of 10-3% by weight. The measuring cell is connected to an electrical comparison circuit which controls a regulator or magnetic valve, in order to control the flow of active chlorine into the system.

Water used for drinking or bathing is primarily sterilized by chlorine, either in gaseous form or in the form of salts of hypochlorous acid. A determining factor of the completeness of sterilization lies in the free, active chlorine content of those chemicals. Free, active chlorine is considerably more effective than bonded (latent) chlorine that has an uncorrelated function in the sterilization process. For swimming pools the optimum concentrations of chlorine is within the narrow range of 0.3 to 0.6 mg/l and should be maintained as accurately as possible within that range.

These values of free, active chlorine must be present in all sections of a swimming pool because of, first, the necessity for disinfection and for sufficiently high oxidation reduction potential being correctly maintained and, second, the avoidance of noxious smells and prevention of eye and mucous membrane irritations as well as of corrosion in water pipes. In prior practice, it has been difficult to maintain the aforementioned values of chlorine continuously at an appropriate uniformity or else at a sufficiently high oxidation reduction potential. The difficulty results from the usual high fluctuations in the number of persons using a swimming pool which is thereby subjected to widely varying contamination loads on the water.

Because of the work load placed on the personnel responsible for the safe and healthy operation of a swimming pool, it has become of utmost necessity that a means be sought to automate the chlorination process.

In the past few years, some devices for automatically chlorinating community swimming pools have become known. Because of the high initial cost associated with these devices, the invention presented here shall be as simple as possible and with that the method of operation shall be so simple that untrained personnel should be capable of continuously monitoring the free active chlorine in order that the installation in private swimming pools might be possible, too.

In the drawing, a direct current source 1 provides current to the two electrodes 3 arranged in the measuring cell 2. These electrodes are flushed by the aqueous solution whose content of free active chlorine is to be measured.

The metallic alloy used in at least one of the electrodes must be of the gold-nickel, gold-copper or gold-iron combination wherein gold is present in a range of about 90 to about 97% gold and about 10 to about 3% of the secondary metal, the preferred embodiment being about 95% gold and about 5% nickel. The gold-nickel alloys show no substantial corrosion under normal usage and is, therefore, preferred. Both electrodes may be of the same, above-mentioned composition.

The direct current source 1 produces a direct current that is sent through the measurement cell 2 and the electrodes 3. The output from cell 2 is sent to circuitry 4. This measured output value first sent to amplifier 5 can be provided in at least one of two ways. First, the voltage $U_1$ can be maintained constant so that the current I from the direct current source 1 flows through the electrodes 3 and the measurement cell 2 (the "amperometric" process). Second, the current I can be maintained at a constant value and the voltage $U_2$ can be measured between the two electrodes 3 (the "coulametric" process). The preferred embodiment uses the amperometric process because the variation in the measuring current I is in linear proportion to the free active chlorine in the system whereas, with the coulametric process, a logarithmic relationship exists between the free chlorine concentration and $U_2$. Therefore, the linearization network 6 shown in the drawing can be omitted when the amperometric measurement process is used, but is preferred when the coulametric process is used.

The linear measuring signal output from 6 is then routed to the comparator 7 for comparison with the reference value provided by reference value adjuster 8. This reference value, represented in the drawing by a unipotential voltage, is calibrated in free chlorine concentration at a selected reference value. If the measured value is lower than the reference value, then the output signal of the comparator 7 actuates the opening of a regulating valve 9 adding chlorine to the system. If the measured value is higher than the reference value, then the output signal brings about the closing of the valve 9. Valve 9 is of a conventional type for controlling the addition of a chlorinating substance from the chlorinator shown and directing it to the pool or other water system.

A series of experimental tests showed the device of this invention operated with stability under the following conditions of use:

| Temperature range | + 1 to +30° C. |
|---|---|
| ph value range | 6.5 to 8.0 |
| Measuring current | $\leq 0.1\ \mu$ Amp |
| Rate of flow | $\geq 1$ m/min |
| Chlorine content: | |

| | |
|---|---|
| free active chlorine | 0.1 mg/l to 2 mg/l |

While the invention herein has been disclosed with reference to certain particular preferred embodiments for illustrative purposes, it will be recognized that variations and modifications of the disclosed apparatus can be made without deviating from the gist of the invention, and such variations and modifications are deemed to fall within the scope of the claims below.

What is claimed is:

1. Apparatus for measuring and monitoring the free chlorine content of aqueous solutions comprising:
   (a) a current source providing current directed to
   (b) at least two electrodes contained in a measuring cell through which a sample of said aqueous solution is flushed, at least one of said electrodes comprising an alloy of gold and metal selected from the group consisting of nickel, copper or iron, wherein gold is contained in an amount of about 90% to about 97% by weight and said nickel, copper or iron is contained in an amount of about 10% to about 3% by weight, the output signal from said electrodes being proportional to the free chlorine content of said aqueous solution, said signal being amplified by
   (c) an amplifier, the amplifier output being sent to
   (d) a comparator for comparison with a reference signal provided by
   (e) a reference value adjuster, the difference in value of the measured signal and reference value being proportional to the free chlorine content in said aqueous system, said difference being used to adjust
   (f) a regulating valve which adjusts the flow of additional chlorine to said aqueous solution.

2. The apparatus of claim 1 including a linearization circuit.

3. The apparatus of claim 1 wherein said electrodes comprise an alloy of gold and nickel wherein the gold content of said electrode is about 95% and the nickel content is about 5%.

4. A process for measuring and monitoring the free chlorine content of an aqueous solution comprising:
   (a) providing a direct current source to at least two electrodes housed in a sample sell, at least one electrode being of the composition, comprising an alloy of gold and a metal selected from the group consisting of nickel, copper or iron, wherein gold is contained in an amount of about 90% to about 97% by weight and said nickel, copper or iron is contained in an amount of about 10% to about 3% by weight,
   (b) flushing said electrodes in said cell with a sample of said aqueous solution,
   (c) amplifying the output signal from said electrodes, this signal being proportional to the free chlorine content of said aqueous solution;
   (d) comparing said amplified signal to an adjustable reference signal, the difference in value of the measured signal and reference value being proportional to the free chlorine content of said aqueous system,
   (e) utilizing said difference to regulate a valve adjusting the flow of additional chlorine to said aqueous solution.

5. The process of claim 4 including linearizing the amplified output signal from said electrodes.

6. The process of claim 4 wherein said electrodes comprise an alloy of gold and nickel wherein the gold content of said electrode is about 95% and the nickel content is about 5%.

* * * * *